United States Patent
Longo et al.

(10) Patent No.: US 12,419,512 B2
(45) Date of Patent: Sep. 23, 2025

(54) METHOD FOR INDUCING A CONTROLLED VARIATION OF ACCOMMODATION IN AN EYE OF A SUBJECT

(71) Applicant: Essilor International, Charenton-le-pont (FR)

(72) Inventors: Adèle Longo, Charenton-le-pont (FR); Camille Cathala, Charenton-le-pont (FR); Gildas Marin, Paris (FR); Martha Hernandez-Castaneda, Charenton-le-pont (FR)

(73) Assignee: Essilor International, Charenton-le-Pont (FR)

( * ) Notice: Subject to any disclaimer, the term of this patent is extended or adjusted under 35 U.S.C. 154(b) by 707 days.

(21) Appl. No.: 17/624,678

(22) PCT Filed: Jul. 2, 2020

(86) PCT No.: PCT/EP2020/068684
§ 371 (c)(1),
(2) Date: Jan. 4, 2022

(87) PCT Pub. No.: WO2021/004891
PCT Pub. Date: Jan. 14, 2021

(65) Prior Publication Data
US 2022/0257109 A1    Aug. 18, 2022

(30) Foreign Application Priority Data
Jul. 5, 2019    (EP) ...................................... 19315061

(51) Int. Cl.
*A61B 3/10*    (2006.01)
*A61B 3/00*    (2006.01)
(Continued)

(52) U.S. Cl.
CPC .......... *A61B 3/0041* (2013.01); *A61B 3/0008* (2013.01); *A61B 3/0091* (2013.01);
(Continued)

(58) Field of Classification Search
CPC ......... A61B 3/1025; A61B 3/02; A61B 3/102; A61B 3/113; A61B 3/1015; A61B 3/1225;
(Continued)

(56) References Cited

U.S. PATENT DOCUMENTS

| | | | | |
|---|---|---|---|---|
| 7,428,001 | B2 * | 9/2008 | Schowengerdt | ..... H04N 13/144 348/E13.067 |
| 2004/0041980 | A1 * | 3/2004 | Laguette | ................... A61B 3/09 351/243 |

(Continued)

FOREIGN PATENT DOCUMENTS

| EP | 2 842 479 A1 | 3/2015 |
|---|---|---|
| EP | 3 298 952 A1 | 3/2018 |

(Continued)

OTHER PUBLICATIONS

Japanese Office Action mailed Apr. 1, 2024 in corresponding Japanese Patent Application No. 2022-500093 (with English translation), 16 pages.

(Continued)

*Primary Examiner* — Dawayne Pinkney
(74) *Attorney, Agent, or Firm* — Oblon, McClelland, Maier &Neustadt, L.L.P.

(57) ABSTRACT

A method for inducing a controlled variation of accommodation in an eye of a subject, using an optical system arranged in front of at least one eye of the subject and including displaying an environmental scene, displaying, in this environmental scene, a target visible by the subject through said optical system, said target being displayed in (Continued)

such a way that it is perceived by the subject as moving away from said subject or moving towards said subject within said environmental scene, having the subject observe said moving target.

13 Claims, 5 Drawing Sheets (51) Int. Cl.
| | | |
|---|---|---|
| A61B 3/02 | (2006.01) | |
| A61B 3/032 | (2006.01) | |
| A61B 3/103 | (2006.01) | |
| A61B 3/12 | (2006.01) | |
| A61B 3/14 | (2006.01) | |
| G02B 27/10 | (2006.01) | |

(52) U.S. Cl.
CPC .............. *A61B 3/032* (2013.01); *A61B 3/103* (2013.01); *A61B 3/145* (2013.01); *G02B 27/10* (2013.01)

(58) Field of Classification Search
CPC ... A61B 3/0025; A61B 3/0058; A61B 3/0091; A61B 3/028; A61B 3/08; A61B 3/09; A61B 3/14; A61B 3/15; A61B 3/152; A61B 3/158
USPC ....... 351/200, 206, 205, 209, 210, 221, 222, 351/246
See application file for complete search history.

(56) References Cited

U.S. PATENT DOCUMENTS

| | | |
|---|---|---|
| 2004/0174499 A1* | 9/2004 | Toshima ................ A61B 3/028 351/239 |
| 2008/0043201 A1 | 2/2008 | Todd |
| 2008/0284979 A1 | 11/2008 | Yee et al. |
| 2011/0279777 A1 | 11/2011 | Yee et al. |
| 2014/0211167 A1 | 7/2014 | Lewis |
| 2016/0045107 A1 | 2/2016 | Welscher et al. |
| 2016/0135677 A1 | 5/2016 | Hawke et al. |
| 2019/0069777 A1* | 3/2019 | Krall ...................... A61B 3/113 |
| 2019/0274539 A1* | 9/2019 | Nauche ................ A61B 3/0041 |

FOREIGN PATENT DOCUMENTS

| | | |
|---|---|---|
| JP | H01-244734 | 9/1989 |
| JP | H11-309114 | 9/1999 |
| JP | 2016-516541 A | 6/2016 |
| JP | 2018-042755 A | 3/2018 |
| JP | 2018-042761 A | 3/2018 |
| KR | 10-2016-0005063 A | 1/2016 |
| WO | WO 2017/050935 A1 | 3/2017 |
| WO | WO 2019/050877 A1 | 3/2019 |

OTHER PUBLICATIONS

International Search Report issued Sep. 7, 2020 in PCT/EP2020/068684, 3 pages.
Aldaba M, et al., "Does the Badal optometer stimulate accommodation accurately?", Ophthalmic Physiol Opt. 2017, 8 pages.
Edgar G., "Accommodation, cognition, and virtual image displays: A review of the literature", Displays., 2007, 15 pages.
Francis E.L., et al. "Accommodation and vergence require effort-to-see", Optom Vis Sci. 2003, 7 pages.
Horwood A. et al., "Receding and Disparity Cues Aid Relaxation of Accommodation", Optometry & Vision Science. 2009, 11 pages.
Ludden S.M., et al. "Children's Accommodation to a Variety of Targets—A Pilot Study", Strabismus. 2017, 23 pages.
McLin L.N. et al. "Changing size (looming) as a stimulus to accommodation and vergence", Vision Res. 1988, 15 pages
Shibata T, et al., "The zone of comfort: Predicting visual discomfort with stereo displays", J Vis. 2011, 29 pages.
Office Action dated Apr. 24, 2025, issued in counterpart CN Application No. 202080048868.2, with English Translation. (18 pages).
Office Action dated Dec. 19, 2024, issued in counterpart KR Application No. 10-2021-7042231, with English Translation. (17 pages).

* cited by examiner

METHOD FOR INDUCING A CONTROLLED VARIATION OF ACCOMMODATION IN AN EYE OF A SUBJECT

TECHNICAL FIELD OF THE INVENTION

The invention relates to a method for inducing a controlled variation of accommodation in an eye of a subject, using an optical system arranged in front of at least one eye of the subject.

BACKGROUND INFORMATION AND PRIOR ART

Devices and methods for limiting the accommodation of the eyes of a subject are used in the context of the determination of refraction features.

During such a determination, it is important to limit accommodation of the eyes that could influence the result of the determination.

Different methods exist, such as the use of a fogging positive lens placed in front of the eye of the patient to induce a myopic situation or the use of cylcopegic eye drops to inhibit accommodation.

However, these methods are uncomfortable for the subject, who remains in a situation of fogged vision for a part of the time of the examination or even longer, in the case of the use of the eye drops.

These eye drops may only be administered by a doctor and present risks of ocular reactions.

Moreover, they do not allow placing the subject in a natural situation of every day life.

SUMMARY OF THE INVENTION

Therefore one object of the invention is to provide a new method for inducing a controlled variation of accommodation in the eye of the subject, in which the subject remains in a visual situation close to every day life, therefore improving the comfort of the subject.

The above objects are achieved according to the invention by providing a method comprising the following steps:
a) displaying an environmental scene,
b) displaying, in this environmental scene displayed in step a), a target visible by the subject through said optical system, said target being displayed in such a way that it is perceived by the subject as moving away from said subject or moving towards said subject, within said environmental scene,
c) having the subject observe said moving target displayed in step b).

Thanks to this method, the accommodation of the subject may be modified to decrease or increase the accommodation while keeping him in a natural vision situation. The observation of a target moving away from the subject allows for the subject to efficiently relax his accommodation. On the contrary, the observation of a target moving towards the subject allows for the subject to efficiently increase his accommodation.

Relaxing the accommodation may be used by itself to relax the subject and provide a break from near vision tasks for example.

It is also useful during determination of the refraction features of the eyes. Usual processes for determining the refraction features are performed in conditions of far vision, with relaxed accommodation, that is with as little accommodation as possible.

The assessment of the visual performance, and therefore determination of the refraction feature, may then be performed after the relaxation of the accommodation, in optimal conditions.

This is particularly useful for subjects naturally accommodating as this is the case for example for young children.

Advantageously, the vision of the subject is not artificially modified by blurring devices such as a fogging lens or a cylcopegic eye drop. The drawbacks linked to the use of these devices are removed.

Increasing the accommodation may be used to place the subject in conditions of accommodation, for example to simulate the state of the eye while achieving a near vision task. This may be useful for example to achieve a vision test in conditions similar to the conditions where the subject has been performing a near vision task.

In both case (relaxation or increase of accommodation), the level of accommodation may be accurately controlled thanks to the method of the invention.

Other advantageous and non-limiting features of the invention are as follows:
said environmental scene is perceived as stationary by the subject while the target is perceived as moving relative to the subject;
in said step b), the angular size of the target displayed is progressively reduced in order for said target to be perceived as moving away by the subject or increased in order for said target to be perceived as moving towards the subject;
in said step b), the position of the target within the environmental scene displayed is modified progressively; in other words, the position of the target relative to the environmental scene is modified;
in said step a), the environmental scene comprises a two-dimensional image or a three-dimensional representation;
in said steps a) and b), at least one of the environmental scene and the target is displayed using a stereoscopic device displaying two overlaid images of said at least one of the environmental scene and target, each image being seen by one of the eyes of the subject and said stereoscopic device introducing a spatial shift between these two images forming together a stereoscopic 3D representation: these two images are two 2D images that form together a 3D representation;
while said at least one of the environmental scene and target is displayed, said spatial shift between the two images of the stereoscopic three-dimensional representation seen by the eyes of the subject is progressively reduced or increased; the effect is to stimulate the convergence or divergence of the eyes of the subject;
one of the two images of the stereoscopic three-dimensional representation is shifted spatially relative to the other of these two images with a spatial shift corresponding to a disparity comprised between 1 and 20 prismatic diopters, this disparity being the same for both environmental scene and target or being different;
while said environmental scene and target are displayed, said disparity is progressively reduced or increased;
said spatial shift is strictly higher or strictly lower than an average spatial shift resulting from the spacing between the eyes of the subject;
said two images of the stereoscopic 3D representation are displayed with two different main color for each eye of the subject or with different polarization for each eye of the subject or thanks to the use of a shutter system;

said target exhibits features with different spatial frequency in order to produce an effective stimulation of the accommodation of the eyes of the subject;

said environmental scene spread over a wide field of view of more than 10 degrees;

said environmental scene comprises a realistic setting having features indicating a situation including different visual distances for a monocular observation by the subject; it comprises preferably a far vision situation for a monocular observation by the subject, at least one of the environment scene, target, musical ambiance, instructions given to the subject before and/or during the step c), is chosen among corresponding environment scenes, targets, musical ambiances, instructions specifically depending on the aging of a subject, and/or of the presbyopia/non presbyopia state of a subject.

The invention also relates to a method for determining at least a refraction feature of an eye of a subject comprising the following steps:

a) displaying an environmental scene,
b) displaying, in this environmental scene displayed in step a), a target visible by the subject through said optical system, said target being displayed in such a way that it is perceived by the subject as moving away from said subject or moving towards the subject,
c) having the subject observe said target moving displayed in step b) and
d) assessing the visual performance of the subject after the subject has observed the target moving in step c),
e) determining said refraction feature based on the assessment of step d).

In practice, at step b), the perception of movement of the target by the subject is obtained by modifying the size of the target relative to the size of the environmental scene, and/or by modifying the position of the target relative to the environmental scene and/or by moving the plane the target is focused and/or by modifying the disparity of the target, and/or by moving the position of the target in space as explained later.

The invention also relates to a global display for inducing a controlled variation of accommodation in an eye of a subject, comprising an environmental scene and a target displayed within this environmental scene, said target being displayed in such a way that it is perceived by the subject as moving away from said subject or moving towards said subject within said environmental scene. This global display may comprise two-dimensional images or three-dimensional representations, as described hereafter.

The wording "display" in "global display" is used here to name "an arrangement of things for people to look at". More specifically, it designates here an arrangement of two-dimensional images and/or three-dimensional representations of an environmental scene and a target.

Said two-dimensional image, hereafter called 2D image, is a classical image displayed on a two-dimensional display. This two-dimensional display is a displaying device for displaying an image in two-dimensions. It may comprise any kind of known displaying device for displaying an image in two-dimensions, such as a screen. The screen may be an active screen, such as a computer screen, or a passive screen, such as a surface for projecting an image. In this last case, the displaying device for displaying an image in two-dimensions also comprises a projection device. This classical 2D image may comprise images of objects having two or three dimensions in space.

Said three-dimensional representation, hereafter called 3D representation, may comprise any kind of representation in three-dimensions such as stereoscopic images and holographic images where the two eyes of the subject don't have the same point of view. It may comprise representations of objects having two or three dimensions in space. It may be displayed by a displaying device for displaying a representation in three-dimensions. It may comprise any kind of known displaying device for displaying a representation in three-dimensions such as a stereoscopic displaying device or a holographic displaying device.

The invention also relates to an optical system for inducing a controlled variation of accommodation in an eye of a subject when arranged in front of at least one eye of the subject, comprising:

a display of an environmental scene,
a display of a target surrounded by the display of said environmental scene and visible by the subject through said optical system,
an optical device for displaying said target in such a way that it is perceived by the subject as moving away from said subject or moving towards said subject within said environmental scene.

The display of the environmental scene and display of a target form a global display. Therefore, here, the display of an environmental scene comprises the arrangement of a two-dimensional image and/or three-dimensional representation of an environmental scene. The display of a target comprises the arrangement of a two-dimensional image and/or three-dimensional representation of a target.

Said optical device therefore comprises:
a displaying device for displaying a two-dimensional image and/or three-dimensional representation of an environmental scene,
a displaying device for displaying a two-dimensional image and/or three-dimensional representation of a target surrounded by said two-dimensional image and/or three-dimensional representation of said environmental scene and visible by the subject through said optical system, in such a way that the target is perceived by the subject as moving away from said subject or moving towards said subject within said environmental scene.

Advantageously, the display of an environmental scene is placed and sized to be visible in a field of view of the subject of at least 10°. In other words, the two-dimensional image and/or three-dimensional representation of the environmental scene is placed and sized to be visible in a field of view of the subject of at least 10°.

Said display of the environmental scene is focused in a first focal plane, said display of the target is displayed in a second focal plane, and said optical device comprises a command unit adapted to command the movement of said first and/or second focal plane in an independent manner, continuously or discontinuously.

In other words, the two-dimensional image and/or three-dimensional representation of the environmental scene is focused in a first focal plane, the two-dimensional image and/or three-dimensional representation of the target is focused in a second focal plane and said optical device comprises a command unit adapted to command the movement of said first and/or second focal plane in an independent manner, continuously or discontinuously.

For example, said global display can be obtained with a device as disclosed in the patent application EP 3298952.

DETAILED DESCRIPTION OF EXAMPLE(S)

The following description with reference to the accompanying drawings will make it clear what the invention consists of and how it can be achieved. The invention is not limited to the embodiment/s illustrated in the drawings. Accordingly, it should be understood that where features mentioned in the claims are followed by reference signs, such signs are included solely for the purpose of enhancing the intelligibility of the claims and are in no way limiting on the scope of the claims.

The method according to the invention allows modifying the accommodation of a subject to decrease or increase the accommodation while keeping him close to a natural vision situation.

Relaxing the accommodation is used by itself to relax the subject and provide a break from near vision tasks for example, or in the context of the assessment of the visual performance of the subject, for example during an eye examination for determining the refraction features of the eye of the subject, by a subjective or an objective method.

Accommodation may indeed prevent an accurate determination of the refraction features of the eyes. In particular, myopia may be overestimated and hyperopia may be underestimated if the eyes of the subject accommodate during the visual test performed to determine the refraction of the eyes.

In order to ensure that the eye is relaxed, that is to say that the accommodation is minimum, it is particularly interesting to perform the method according to the invention for controlling accommodation and decreasing it before determining the refraction features of the eyes. The prescription may then be more accurate and the equipment better tolerated.

Increasing the accommodation may also be useful in the context of visual tests for determining refraction features of the eyes in conditions of near vision task.

In both case (decrease or increase of accommodation), the level of accommodation may be accurately controlled thanks to the method of the invention.

More precisely, according to the invention, the method for inducing a controlled variation of accommodation in an eye of a subject, using an optical system arranged in front of at least one eye of the subject and comprising the following steps:
 a) displaying an environmental scene,
 b) displaying, in this environmental scene displayed in step a), a target visible by the subject through said optical system, said target being displayed in such a way that it is perceived by the subject as moving away from said subject or moving towards said subject within said environmental scene,
 c) having the subject observe said moving target displayed in step b).

Step a)

An environmental scene is displayed. This scene comprises a 2D image or 3D representation that may be a photograph or a digitally created picture or a hand drawn picture.

Figure 1:
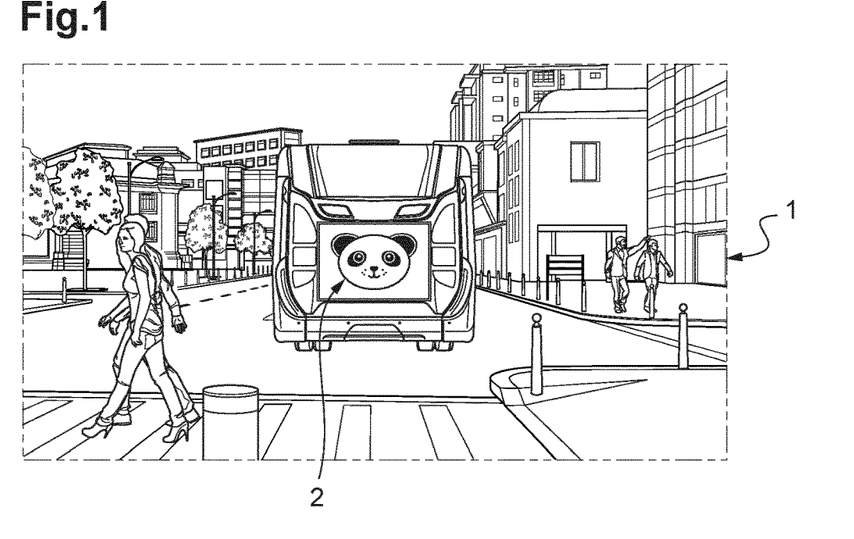
FIG. 1 is a schematic view of an environmental scene comprising a target used in the methods according to the invention.

An example of such an environmental scene 1 is shown on FIG. 1.

Preferably, the environmental scene 1 is a realistic one.

It preferably represents a scene of every day life for the subject. This scene may therefore be personalized based on the habits of the subject, for example based on the country where he lives or the environment: city/countryside for example, where he lives.

For example, it may show a rural landscape, a mountain landscape or a seaside landscape. In particular, it may show a city landscape, as visible on the examples shown on the appended figures.

No matter which specific scene is chosen, it preferably comprises features indicating distances in monocular vision. It preferably also corresponds to a large visual field. The environmental scene 1 is preferably displayed over a visual field of more than 10° at least horizontally.

Figure 9:
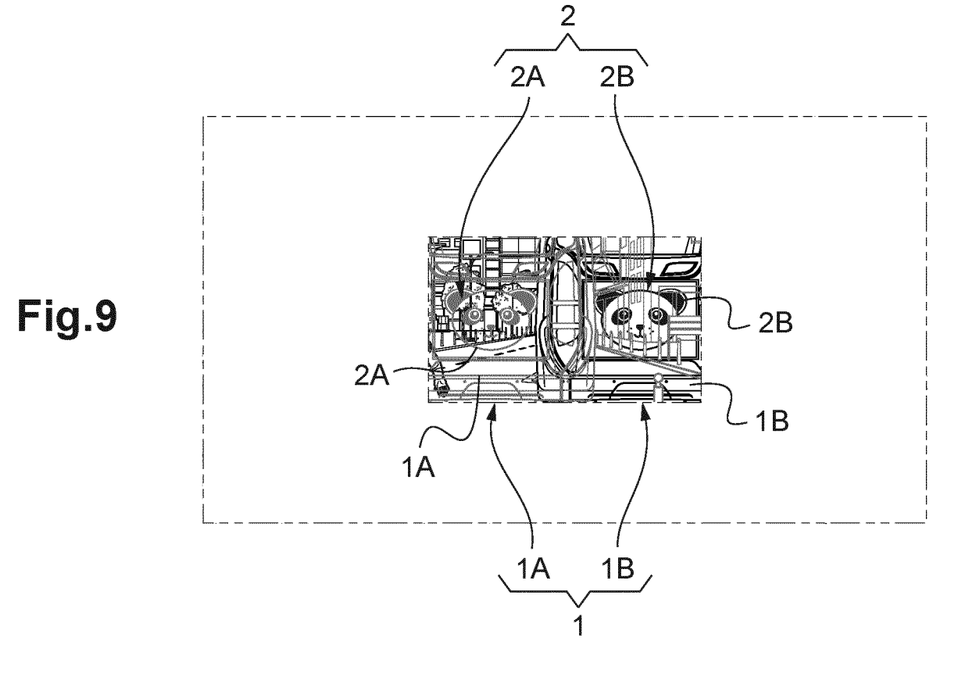
FIGS. 9 and 10 are schematic views of the environmental scene and target used in the methods according to the invention FIGS. 9 and 10 showing said target at two different moments during the achievement of yet another embodiment of the method according to the invention, the scene and target being displayed as 3D representation comprising two images of the scene 1A, 1B and two images of the target 2A, 2B, one of each of the two images of the scene 1A, 1B and one of the two images of the target 2A, 2B being represented with black lines and the others with gray lines.
Figure 10:
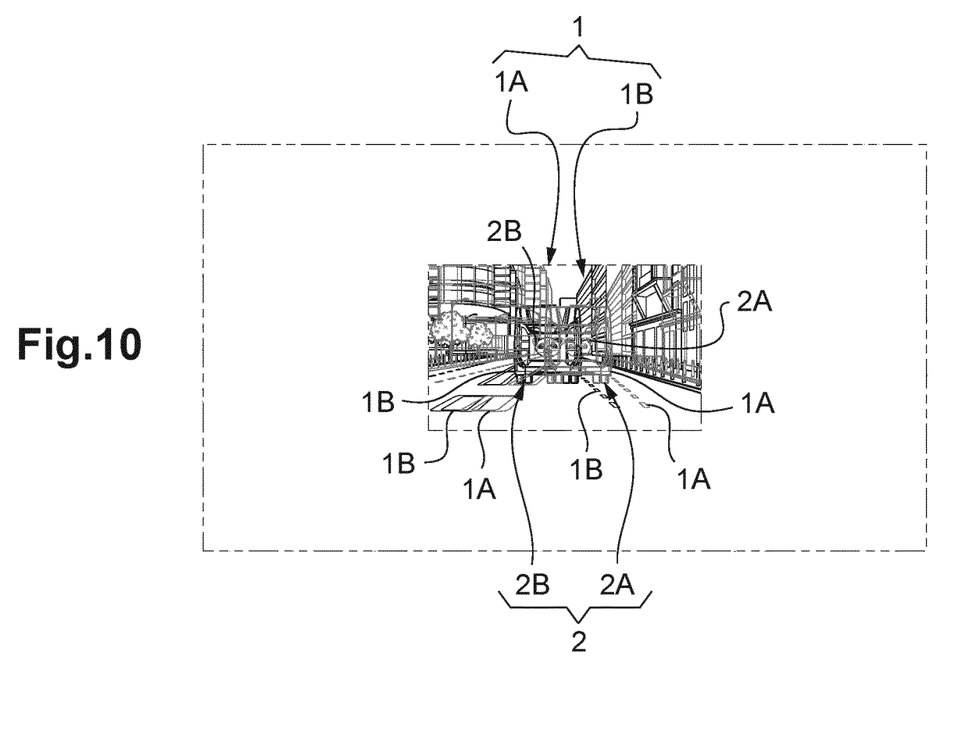

This is for example the case of the environmental scene displayed on FIG. 1, which exhibit a visual field of 32° (horizontal) by 19.37° (vertical). As a comparison, FIGS. 9 and 10 show a reduced visual field of 11.37° (horizontal) by 6.68° (vertical).

The features indicating distances in monocular vision comprise typically elements of known real height for the subject, for example trees or buildings, road, persons, vanishing lines and/or vanishing points.

Vanishing lines are present in the example shown in the building and the road markings.

The features indicating distances in monocular vision may suggest far vision, intermediate vision or near vision, depending on the scene displayed.

Such features indicating distances in monocular vision comprise for example shadows, repeating patterns, objects of known size in real life.

The urban scene, as shown on the examples of the figures comprises numerous indicators of distances in monocular vision with a large field of view and elements of every day life.

The environmental scene comprises different colors with many shades of grey.

The environmental scene may be a two-dimensional or a three-dimensional representation.

As mentioned before, said two-dimensional image, hereafter called 2D image, is a classical image displayed on a two-dimensional display, that is to say, a displaying device for displaying an image in two dimensions. This classical 2D image may comprise images of objects having two or three dimensions in space.

Said three-dimensional representation, hereafter called 3D representation, may comprise any kind of representation in three-dimensions such as stereoscopic images and/or holographic images. It may comprise representations of objects having two or three dimensions in space. This environmental scene remains preferably stationary during the implementation of the method: it comprises a fixed 2D image or a fixed 3D representation relative to the subject.

This is to allow the attention of the subject to be focused on the target described hereafter.

Alternatively, the environmental scene may comprise at least one moving element other than the target. It may be animated. It may comprise a video sequence or a plurality of 2D images or 3D representations.

Step b)

In this environmental scene 1 displayed in step a), a target 2 visible by the subject through said optical system is displayed.

According to the invention, this target comprises a 2D image or 3D representation of a sign.

This sign preferably exhibits different spatial frequencies. This allows stimulating the visual system of the subject as a whole and in particular the accommodative system of the eye, even if the size of the target varies, and in particular decreases.

The sign may comprise an optotype or a 2D image or 3D representation of an object or an image of a character, a plurality of 2D images or 3D representations, a video, a drawing or a photograph.

In particular, said target may comprise a 2D image or 3D representation.

The target presents different spatial frequencies because it has components of different sizes. Examples of the target 2; 3 are shown on FIGS. 2 and 3.

Figure 2:
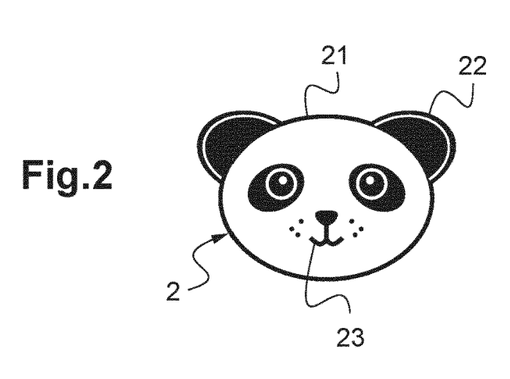
FIG. 2 is a schematic view of a first example of target used in the methods according to the invention, corresponding to the target of FIG. 1.

For example, for a given distance of observation between the subject and the target, the width of the line circling the ear of the panda on FIG. 2 corresponds to a visual acuity of 5/10 whereas the width of each eye of the panda corresponds to a visual acuity of 2.5/10. Moreover, when the panda is moving away on FIG. 3, the width of the line circling the ear of the panda corresponds to a visual acuity of 16/10 whereas the width of each eye of the panda corresponds to a visual acuity of 8/10.

Figure 3:
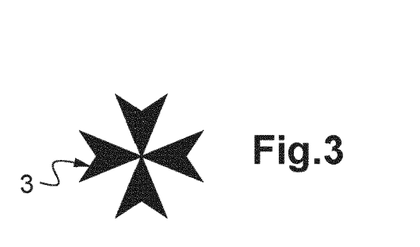
FIG. 3 is a schematic view of a second example of target used in the methods according to the invention.

The target 2; 3 is preferably represented in black and white. This ensures an appropriate contrast for the target to stimulate the accommodation system of the eyes and the attention of the subject. It also allows an easier display, that is to say, an easier exhibition, with dissociation of the binocular vision thanks to different colors such as red and green, as described later, while minimizing the risk of retinal rivalry due to the colors.

An example of target 2 presents here the shape of the head of a panda (FIG. 2).

Alternatively, it could comprise for example a smiley or the head of a clown.

Using such a target may help attracting the attention of young children.

Optionally, a blinking target may also be used to stimulate the attention of the subject.

It comprises lines of different widths, such as the lines 21, 22, 23 of the target 2 representing the shape of the head of the panda (FIG. 2).

This target 2 comprises parts of a first size, such as the ears of the panda, and parts of a second size, such as the eyes of the panda. Finer parts, such as the mouth and the points placed besides the mouth of the panda are also provided.

The example of the target 3 represented on FIG. 3 comprises a cross, with four arms having a first spatial frequency, each divided in two arrows having a second spatial frequency.

The parts with lower spatial frequency, that is to say, the bigger features of the target, play an important role in stabilizing and guiding the global accommodation of the eyes of the subject. The finer parts of the target having a higher spatial frequency relative to the parts with lower spatial frequency, play a role in fine tuning the accommodative response.

Other kind of targets can of course be used, ideally comprising one or more of the above optimized feature(s) playing a role in fine tuning the accommodative response such as different spatial frequencies, components of different sizes, black and white representation, a form adapted to the age of the subject, associated relaxing sounds or musical ambiance, or any other features known by the skilled man as stimulating the accommodative system of a subject even if the size of the target decreases.

The subject observes a global display comprising overlaid 2D images or 3D representations of the environmental scene 1 and target 2.

According to the invention, said target is displayed in such a way that it is perceived by the subject as moving away from said subject or moving towards said subject within said environmental scene.

Preferentially, said environmental scene is perceived as stationary by the subject while the target is perceived as moving relative to the subject.

By concentrating the attention of the subject on a target perceived as moving, it is possible to control the accommodation of the eyes of the subject by progressively modifying the accommodation along with the perceived movement of the target. This perception of movement may be obtained through any of the means described here. A target perceived as moving towards the subject will induce an increasing accommodation in the eyes of the subject, whereas a target perceived as moving away from the subject will induce a decrease of the accommodation of the subject.

In order to give to the subject the impression that the target is moving away or towards him, it is possible to use different global displays and optical systems corresponding to different embodiments of the method according to the invention.

A first embodiment of the method uses a first global display and implies modifying the angular width of the target 2.

Then, in said step b), the angular size of the target displayed is progressively reduced in order for said target to be perceived as moving away by the subject or increased in order for said target to be perceived as moving towards the subject.

Figure 4:
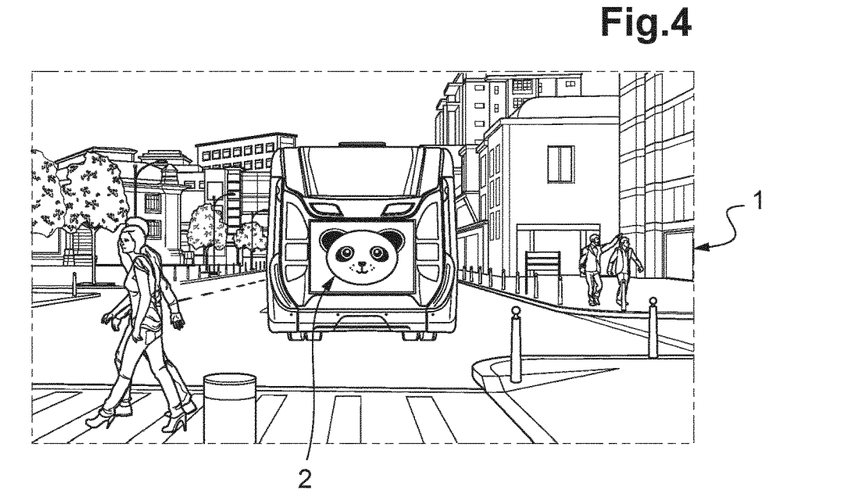
FIGS. 4 and 5 are schematic views of the environmental scene and target used in the methods according to the invention, FIGS. 4 and 5 showing said target at two different moments during the achievement of a first embodiment of the method according to the invention.
Figure 5:
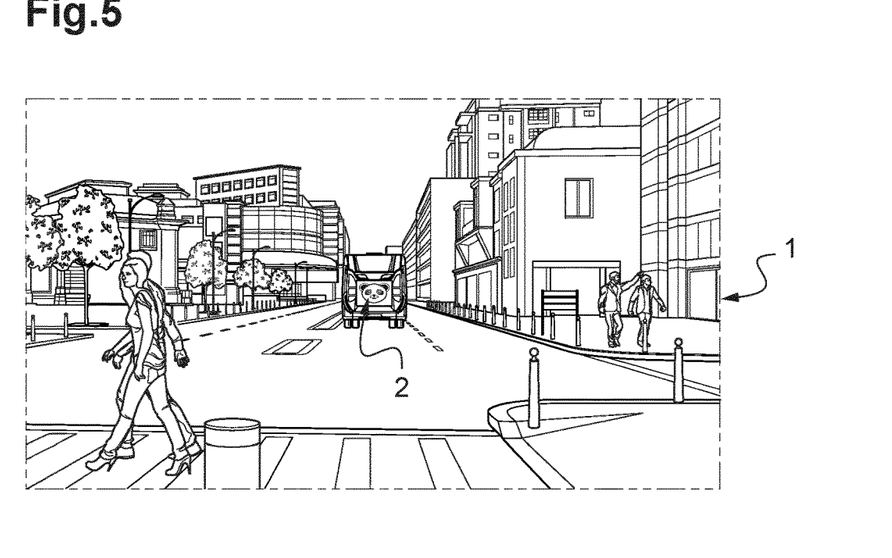

The position of the center of the target 2 remains fixed at the same position within the environmental scene 1 (FIGS. 4 and 5). The angular width, in other words, the size, of the target, is increased or decreased homothetically. In other words, the size of the target is modified without deformation of the target.

An example of a global display used in this first embodiment is shown on FIGS. 4 and 5. FIG. 4 shows the target 2 inside the environmental scene 1 at the beginning of the observation of the subject, and FIG. 5 shown the target 2 inside the environmental scene 1 at the end of the observation of the subject.

The increase of the angular width suggests the perception of the target moving towards the subject, whereas the decrease of the angular width suggests the perception of the target moving away from the subject.

In the example of FIGS. 4 and 5, the size of the target 2 is decreased, the target 2 is perceived as moving away from the subject.

The modification in the size of the target induces a modification in accommodation of the eyes of the subject, followed by a modification in the vergence of the eyes.

This first embodiment of the method may be implemented with target and environmental scene displayed as 2D images or 3D representations.

The environmental scene is preferably stationary. It comprises preferably a fixed 2D image or 3D representation. The target may also be displayed by a sequence of fixed 2D images or 3D representation, or 2D or 3D videos: the size of the target is then modified in a discontinuous manner or by a video: the size of the target is then modified continuously.

A second embodiment of the method using a second global display implies moving the target within the environmental scene.

In the case where the environmental scene and target comprise 2D images, the 2D image of the target is moved within the 2D image of the environmental scene, that is, in the plane of this 2D image of the scene. The position of the target relative to the fixed 2D image forming the environmental scene is modified.

In the case where the environmental scene and target comprise 3D representations, the 3D representation of the target is moved within the 3D representation of the environmental scene, that is, relative to the fixed 3D representation forming the environmental scene.

In said step b), the position inside the environmental scene 1 of the target 2 displayed is modified progressively.

A movement of the target towards the upper region of the environmental scene (corresponding, for example, to the image of the sky on FIG. 1), suggests a movement of the target away from the subject, whereas a movement of the target towards the lower region of the environmental scene (corresponding, for example to the pedestrian crossing in FIG. 1), suggests a movement of the target towards the subject.

Upper and lower region of the scene are here defined relative to the vertical direction for the subject in conditions for observing the scene.

This second embodiment may use target and environmental scene in two or three dimensions that is to say displayed as 2D images or 3D representations.

The environmental scene is preferably stationary. It comprises preferably a fixed 2D image or 3D representation. The target may be displayed by a sequence of fixed 2D images or 3D representations: the position of the target is then modified in a discontinuous manner, or by a video: the position of the target is then modified continuously.

A third embodiment of the method according to the invention uses an third global display (not represented on the figures) and implies modifying the distance between a focal plane in which the target 2 is displayed and the subject. In this last case, the distance in space between the subject and the target 2 is actually modified.

A focal plane placed at infinity from the subject corresponds to no accommodation of the eyes. A focal plane placed at a reading distance from the subject (for example 40 centimeters), corresponds to an accommodation of 2.5 diopters.

The environmental scene may comprise a 2D image or 3D representation.

The environmental scene is preferably stationary. This avoids disturbing the attention of the subject from the target. It comprises preferably a fixed 2D image or 3D representation. The focal plane of the environmental scene 1 is therefore preferably fixed, that is to say not modified during the performance of the method according to the invention.

In the case where the environmental scene is a 2D image, the subject therefore observe the target with a focal plane progressively modified surrounded by the environmental scene with a fixed focal plane. The position of the focal plane in which the target is focused is moved along the gaze direction of the subject. As a variant, the focal plane of both target and environmental scene may be modified.

In this case, the focal plane of both target and environmental scene are move in an independent manner. They are moved continuously or discontinuously over a range of distance to the subject.

An optical device is used to modify the focal plane of the target. This optical device comprises for example lenses with a variable position relative to the subject and/or with a variable focal distance. It may for example comprise at least a lens slidably mounted on a rail, as a Badal system.

In the case where the environmental scene is a 3D representation, the subject therefore observe the target with a focal plane progressively modified surrounded by the unchanged environmental scene.

In the case where the target and environmental scene comprise 3D representation, the position of the target along the gaze direction of the subject may be modified inside the 3D representation of the environmental scene. The position in space of the target relative to the subject is then modified.

More precisely, the distance between the target and the subject along the gaze direction of the subject is modified, shortened or lengthened, depending on the direction of the movement of the target towards or away from the subject.

The target may be displayed by a sequence of fixed 2D images: the focal plane of the target is then modified in a discontinuous manner or by a video: the focal plane of the target is then modified continuously.

These three embodiments and/or set-ups may be combined, and we can for example consider modifying the distance between the subject and the focal plane of display of the target, that is to say, the focal plane of exhibition of the target, while simultaneously modifying the angular width of the target and/or modifying the position of the target inside the environmental scene.

No matter which embodiment is performed or which set-up is used, it is advantageous to integrate the target into a realistic setting of the environmental scene.

In the case of the examples shown on the figures, the target is placed at the back of a bus centered in the environmental scene (FIG. 1).

The environmental scene then comprises a bus going away from the subject.

In the example shown on FIGS. 4 and 5, the bus is perceived as going away at a speed of 7.5 kilometers per hour.

The distance as perceived between the subject and the target is modified from 10.34 meters (FIG. 4) to 31.19 meters (FIG. 5).

This distance is a psychologic distance as perceived by the subject and not a real focusing distance.

As a consequence, the sizes of the features of the target are modified.

While the width of the line circling the ear of the panda shown on the target 2 corresponds to a visual acuity of 5/10 on FIG. 4, this width decreases to correspond to a visual acuity of 16/10 on FIG. 5. The width of each eye of the panda corresponding initially to a visual acuity of 2.5/10 (FIG. 4) corresponds then to a visual acuity of 8/10 on FIG. 5.

A fourth embodiment using a fourth global display uses a dissociation of the binocular vision.

It is based on using a stereoscopic device for displaying at least the target 2 in a stereoscopic 3D representation.

In real life, because of the eyes' horizontal separation, the two eyes of the subject have a different point of view on any scene observed by the subject. The difference in the point of view of the eyes creates a binocular disparity that the brain uses to extract depth information from the combination of two two-dimensional retinal images.

Binocular disparity refers to the difference in position of an object seen by the left and right eyes during binocular observation of this object. In practice, it is representative of the distance between two corresponding points in the left and right image of a stereo pair, reflecting the difference in image location of an object seen by the left and right eyes resulting from the eyes' horizontal separation.

A similar difference in point of view is simulated in a stereoscopic 3D representation by creating two images differing from each other by a difference in point of view corresponding to a predetermined disparity, each of them being displayed to one of the eye of the subject. In this fourth embodiment, at least one of the environmental scene 1 and the target 2 is displayed using a stereoscopic device displaying two overlaid images 1A, 1B, 2A, 2B of said at least one of the environmental scene and target, each image being seen by one of the eyes of the subject, said stereoscopic device introducing a spatial shift between these two images 1A, 1B, 2A, 2B forming together said stereoscopic three-dimensional representation.

While said at least one of the environmental scene 1 and target 2 is displayed, said spatial shift between the two images of the stereoscopic three-dimensional representation seen by the eyes of the subject is progressively reduced or increased.

This spatial shift is a shift along the direction of the axis linking the eyes of the subject.

For example, the target 2 is thus displayed using two different images 2A, 2B for the right and left eyes. In this case, the 3D representation of the target comprises the two overlaid images of the stereoscopic 3D representation.

The difference between these two images, and therefore, said spatial shift between the two images of the stereoscopic 3D representation, may be quantified by a disparity of the 3D representation.

The disparity may be quantified in prismatic diopters.

The disparity of the stereoscopic 3D representation is comprised between 1 and 20 prismatic diopters. This disparity may be the same for both environmental scene 3D representation and target 3D representation or may be different.

One of the images of the stereoscopic 3D representation then corresponds to the other image of the stereoscopic 3D representation through a prism of disparity comprised between 1 and 20 prismatic diopters.

The disparity of the stereoscopic 3D representation of any object in the 3D representation is determined based on the actual distance between this object of the subject in real life and on the interpupillary distance of the subject. The disparity is typically larger for objects that are closer to the subject than for the objects that are further away.

Therefore, the disparity of the 3D representation forming the target 2, that is to say, the spatial shift between the two images 2A, 2B forming the stereoscopic 3D representation of the target 2, may be progressively modified in order to suggest the movement of the target.

In practice, while said target 2 is displayed, said disparity, that is to say said spatial shift, between the two images of the stereoscopic three-dimensional representation seen by the eyes of the subject is progressively reduced or increased.

Optionally, the environmental scene 1 may also be displayed with a stereoscopic 3D representation. This is to bring other distances perception indicators. The environmental scene 1 is then displayed with two overlaid images 1A, 1B. The disparity of the stereo image forming the environmental scene 1 may also be varied in time and/or in space within the stereo image.

Having portions of the stereo image with different disparities increases the perception of the scene as realistic, as different depths are perceived thanks to the different disparities.

Said disparity may either be a crossed or an uncrossed disparity, as detailed hereafter. The use of crossed or uncrossed disparities between the two images of the stereoscopic 3D representation may enhance the convergence or divergence of the eyes obtained.

When displaying one of the two images of the stereoscopic 3D representation of the target 2 and, optionally, of the environmental scene 1, the spatial shift between the two images implies that one of them appears shifted to the left and the other appears shifted to the right of the subject.

When the image placed on the left of the subject is displayed to his left eye and the image placed on the right of the subject is displayed to his right eye, the disparity between the two images is called uncrossed, and the resulting stereoscopic 3D representation appears to be away from the subject, in particular further away from the plane of the two overlaid images.

When the image placed on the left of the subject is displayed to his right eye and the image placed on the right of the subject is displayed to his left eye, the disparity between the two images is called crossed, and the resulting stereoscopic 3D representation appears to be close to the subject, in particular in front of the plane of the two overlaid images.

Consequently, the crossed disparity of the target 2 may be increased in order for the target to be perceived as moving towards the subject, therefore stimulating the convergence of the eyes and an increase in the accommodation of the eyes, and the uncrossed disparity of the target may be increased in order for the target to be perceived as moving away from the subject, therefore stimulating the divergence of the eyes and a decrease of the accommodation of the eyes.

Therefore, the variation of the disparity of the target 2 may comprise an increase of the uncrossed disparity or a decrease of the crossed disparity, in order for the target to be perceived as moving away from the subject, therefore stimulating the divergence of the eyes. The variation of the disparity may also comprise an increase of the crossed disparity or a decrease of the uncrossed disparity in order for the target to be perceived as moving towards the subject, therefore stimulating the convergence of the eyes.

Stimulating convergence/divergence of the eye will automatically stimulate an associated accommodation/un-accommodation since both are linked physiologically, so stimulating convergence/divergence induces stimulating accommodation.

The wording "disparity" is used in the present description as a generic word meaning crossed or uncrossed disparity.

The target 2 itself is not modified in size or position.

Figure 6:
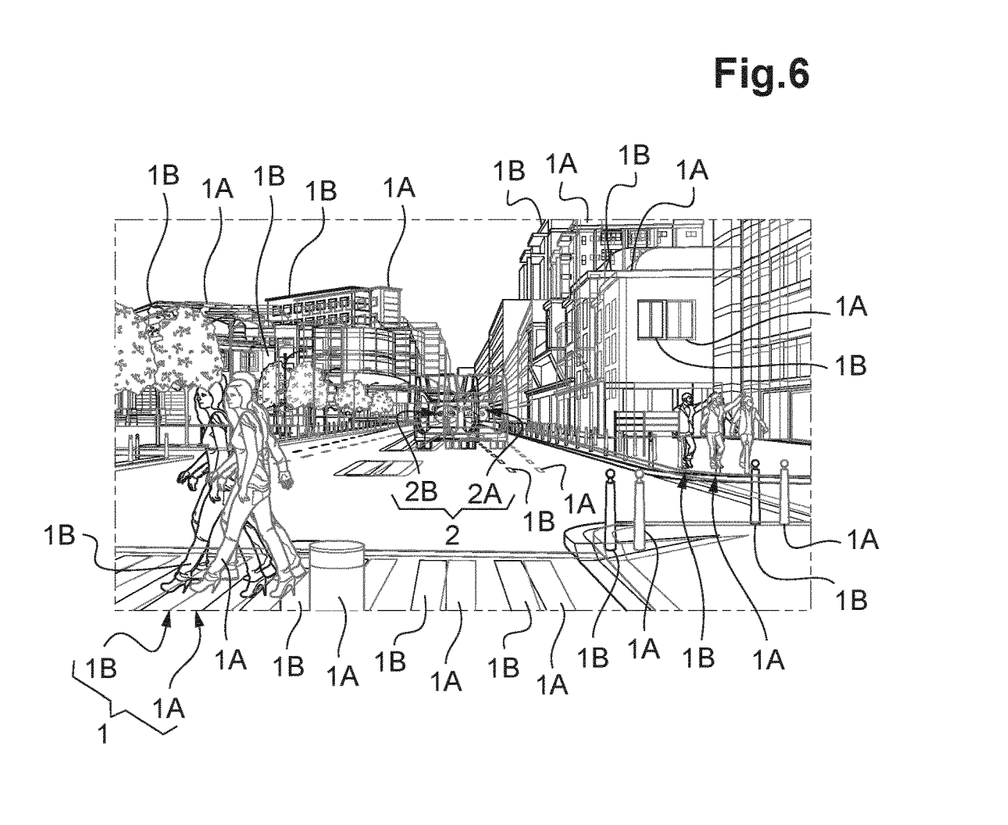
FIG. 6 is a schematic view of the environmental scene and target used in the method according to the invention, wherein only the disparity of the target is varied, the scene and target being displayed as 3D representation comprising two images of the scene 1A, 1B and two images of the target 2A, 2B, one of each of the two images of the scene 1A, 1B and one of the two images of the target 2A, 2B being represented with black lines and the others with gray lines.

This case is schematically represented at a moment in time on FIG. 6. On FIG. 6, the environmental scene and the target are displayed as stereoscopic 3D representations comprising two images of the scene 1A, 1B and two of the target 2A, 2B. One of each of the two images of the scene 1A, 1B and one of the two images of the target 2A, 2B is displayed for each eye. As an example, the images 1A, 2A of the scene and target are for example displayed to the right eye with a red dominant color, whereas images 1B, 2B of the scene and target are displayed with a green dominant color to the left eye.

During the display of the target in the embodiment of FIG. 6, that is to say, during the exhibition of the target, the disparity of the target 2 is modified, here decreased, but the size and position of the target remain the same. In practice, it means that while displaying the global display comprising the environmental scene and target, the distance between the two images 2A, 2B of the 3D representation of the target 2 is varied. Here, as the disparity is decreased, the two images 2A, 2B of the 3D representation of the target 2 moves towards each other to become closer if image 2A is seen by the right eye of the subject and image 2B is seen by the left eye (the contrary if eyes are reversed).

In the case where the disparity is increased, the two images 2A, 2B of the 3D representation of the target 2 move apart so that the distance between the two images 2A, 2B increases.

Alternatively, it is possible to consider varying both the disparity, that is to say said crossed or uncrossed disparity of the target, and the size and/or position and/or focal plane of the target.

In the case where both the target and environmental scene are displayed with stereoscopic 3D representations, the disparity of the stereoscopic 3D representation showing the environmental scene may be the same as the disparity of the stereoscopic 3D representation showing the target, or it may be different. The disparity of the stereoscopic 3D representation showing the environmental scene may be modified in the same way as the disparity of the stereo image showing the target, or it may be modified differently.

However, preferably the disparity of the stereo image showing the environmental scene remains the same during the display, that is to say, the exhibition of the environmental scene.

The disparity may here be created virtually as if using two image capture devices to capture two images of the environmental scene and target with two different point of view.

The spatial shift between the two image capture devices is about 63 millimeters, corresponding to the average interpupillary distance of human beings.

In a variant, at least during a period of time during which the target is displayed, said spatial shift is strictly higher or strictly lower than an average spatial shift resulting from the spacing between the eyes of the subject.

The disparity introduced between the two images of the stereoscopic 3D representation seen by each of the subject's eye is determined based on the amount of convergence or divergence looked for in order to stimulate the eyes of the subject.

The value of the disparity introduced between the two images may take into account average values for a predetermined population of subjects and/or may be adapted to the subject. For example, geometrico-morphological parameters of the subject, such as the interpupillary distance of the subject, and physiological parameters, such as his capacity to avoid double vision when shown stereo images with high disparity and/or his maximum remaining capacity of accommodation (that may be estimated by a relation to the age) may be taken into account.

Alternatively, the convergence/divergence may be exaggerated to force the resulting stimulation of accommodation/un-accommodation. The wording "un-accommodation" is used here as meaning a "decrease of the accommodation".

For example the disparity may create a disparity larger than the interpupillary distance creating a divergence higher than for infinity, forcing stimulation of un-accommodation For a given predetermined convergence or divergence looked for, the disparity introduced and the features of the global display as a whole are adapted based on the distance between the subject's eye and the 2D image or 3D representation displayed, as well as on geometrico-morphological parameters of the subject, such as the interpupillary distance of the subject.

The level of maximum convergence and/or divergence that can be obtained using a given set-up depends on the distance between the subject and the focalization plane, and/or on the physiological features of the subject, such as his capacity to avoid double vision when shown stereo images with high disparity.

The value of the convergence and/or divergence looked for may be deduced from databases defining the average zone for simple and focused vision in a given population.

For example, in far vision, a maximum convergence mean value is 3 prismatic diopters, and a maximum divergence mean value is 1 prismatic diopter.

The disparity of the stereo images is here achieved thanks to displaying images with different dominant colors of each eye. The image displayed for the right eye is mostly red, whereas the image displayed for the left eye is mostly green.

The subject wears glasses with corresponding colored lenses.

Here, said two images are displayed for each eye of the subject with two different main colors. Alternatively, they may be displayed with different polarizations or thanks to the use of a shutter system.

The dissociation of the binocular vision encourages the relaxing or the increase of the accommodation by decoupling accommodation and convergence.

This kind of set-up is well accepted from subjects.

This fourth embodiment may be combined with other embodiments.

Figure 7:
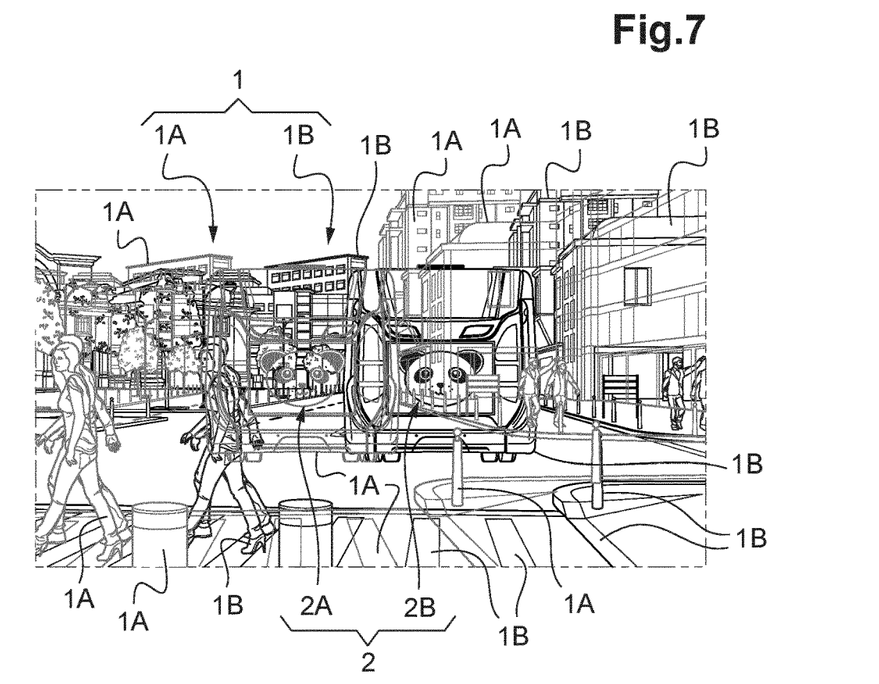
FIGS. 7 and 8 are schematic views of the environmental scene and target used in the methods according to the invention, FIGS. 7 and 8 showing said target at two different moments during the achievement of another embodiment of the method according to the invention, the scene and target being displayed as 3D representation comprising two images of the scene 1A, 1B and two images of the target 2A, 2B, one of each of the two images of the scene 1A, 1B and one of the two images of the target 2A, 2B being represented with black lines and the others with gray lines.
Figure 8:
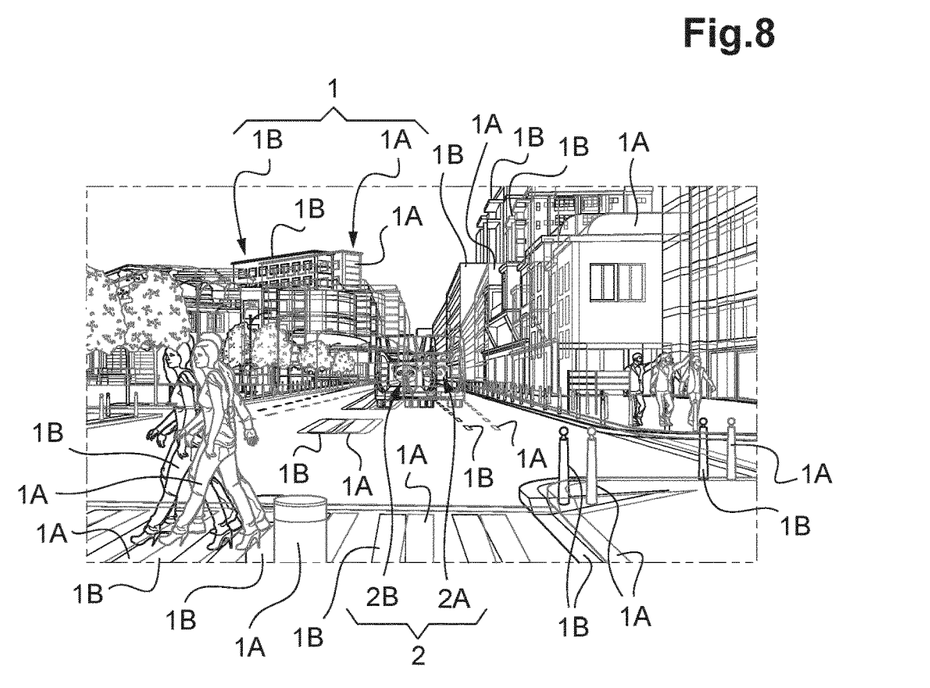

In the example shown on FIGS. 7 and 8, the target 2 and environmental scene 1 are displayed with the same disparity. They are displayed as stereoscopic 3D representations comprising two images of the scene 1A, 1B and two images of the target 2A, 2B. One of each of the two images of the scene 1A, 1B and one of the two images of the target 2A, 2B is displayed to each eye. As an example, the images 1A, 2A of the scene and target are for example displayed to the right eye with a red dominant color, whereas images 1B, 2B of the scene and target are displayed with a green dominant color to the left eye.

The angular size of the target 2 in said 3D representation is progressively decreased and the uncrossed disparity is progressively increased accordingly in order for the target 2 to be perceived by the subject observing it as moving away from him as in a realistic situation.

FIG. 7 shows schematically the two overlaid images of the 3D representation of the environmental scene 1 with the two overlaid images of the 3D representation of the target 2 as shown at the beginning of the performance of the method. FIG. 8 shows schematically the two overlaid images of the 3D representation of the environmental scene 1 with the two overlaid images of the 3D representation of the target 2 as shown at the end of the performance of the method: the angular size of the target 2 is smaller than on FIG. 7, and the disparity of both environmental scene and target is smaller than on FIG. 7.

In the example of FIG. 7, the disparity is of 15.35 prismatic diopters in convergence, whereas on FIG. 8, it is of 3.2 prismatic diopters in divergence.

The disparity value may be determined based on the geometrico-morphological and/or physiological parameters of the subject. In that case, these parameters are determined, for example measured, in a preliminary step.

The example shown on FIGS. 9 and 10 is similar to the example of FIGS. 7 and 8, except that the global display extends over a smaller field of view.

Figure 11:
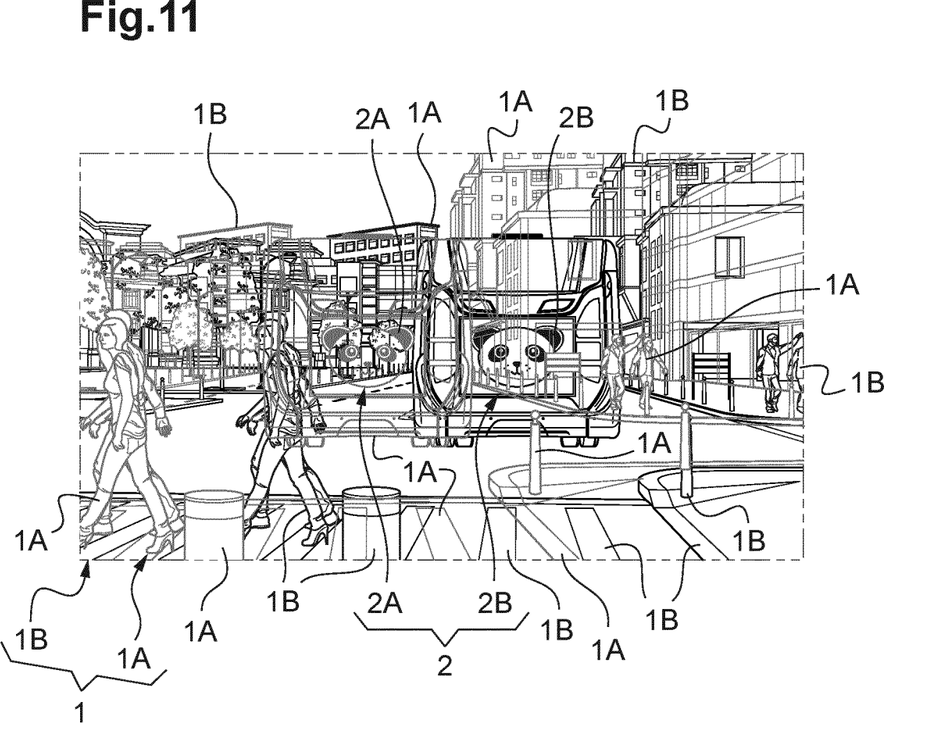
FIGS. 11 and 12 are schematic views of the environmental scene and target used in the methods according to the invention, FIGS. 11 and 12 showing said target at two different moments during the achievement of a last embodiment of the method according to the invention, the scene and target of FIG. 11 being displayed as 3D representation comprising two images of the scene 1A, 1B and two images of the target 2A, 2B, one of each of the two images of the scene 1A, 1B and one of the two images of the target 2A, 2B being represented with black lines and the others with gray lines.
Figure 12:
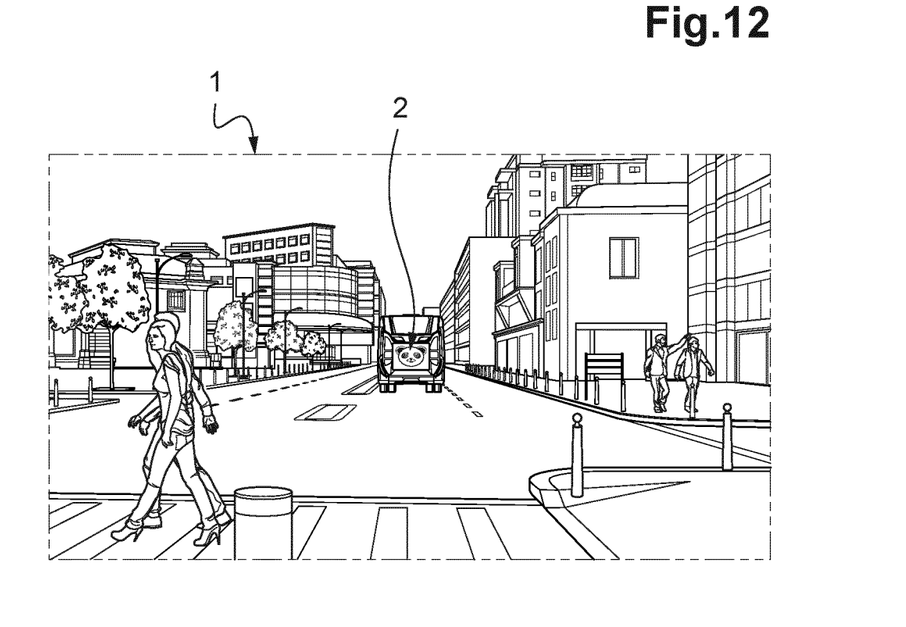

In the example shown on FIGS. 11 and 12, the target and environmental scene are displayed with the same disparity. The angular size of the target 2 is progressively decreased and the disparity is progressively decreased accordingly in order for the target 2 to be perceived by the subject observing it as moving away from him, down to a zero disparity or a divergence demand.

FIG. 11 is similar to FIG. 7. It shows the environmental scene 1 with the target 2 as shown at the beginning of the performance of the method. The target 2 has an initial size and the target 2 and environmental scene 1 are displayed with an initial disparity. FIG. 12 shows the environmental scene 1 with the target 2 as shown at a later stage of the performance of the method: the angular size of the target 2 is smaller than on FIG. 11, and no disparity is present. In this case, both the angular size and the disparity of the 3D representation of the target 2 are decreased while displaying the global display to the subject.

Step c)

In step c), the subject observes the global display comprising overlaid 2D images or 3D representations of the environmental scene 1 and target 2.

This observation induces a controlled modification of the accommodation of the eyes of the subject.

To even more control the accommodation of the eyes of the subject, the age of the subject and/or his/her level of attention, and/or body relaxation and stereoscopic disparities sensitiveness can be taken into account.

More precisely, experiments were carried out on different subjects (presbyopic and non presbyopic people) by measuring accommodation in real time (10 Hz) under different conditions with a Grand Seiko device (WAM 5500). These measurements were made in order to test whether the attention, the types of targets used and the physical excitation (after sport) or relaxation of the subject influences his accommodation. The tested conditions were:

white background, forest background, or city background for the environment scene, before implementing the test, using a video with an unpleasant punching noise or the same video with a sound of birds for the musical ambiance of the test, before implementing the test, asking the subject to be attentive, to count mentally from 200 to 0 by step of 3 to 3, or to click with the help of a digital pad for focusing his/her attention, implementing the test after 2 minutes of relaxation or after a physical exercise that consisted of going up and down 4 floors running for promoting his/her body relaxation, using targets with & without stereoscopic disparities.

From these experiments, it appears that realistic scenes (forest, natural landscape background, or city background) for the environment scene and even more, binocular 3D environment scene condition, help to maintain relaxed accommodation for all types of subjects.

For young people or non-presbyopic people, asking to relax (or showing forest as the environment scene or listening to relaxing or natural sounds like bird sounds/videos) helped to relax accommodation.

For presbyopic people, asking to be more attentive orally, or by using a digital pad helped to relax accommodation.

Therefore at least one of the environment scene, target, musical ambiance, instructions given to the subject before and/or during the step c) (to pay attention, to use a pad . . . ), can advantageously be chosen among corresponding environment scenes, targets, musical ambiances, instructions, specifically depending on the aging of a subject, and/or of the presbyopia/non presbyopia state of a subject to promote accommodation relaxation.

Thus, having a control of attention and relaxation depending of the aging of the patient and/or his/her presbyopia/non presbyopia is beneficial to control accommodation relaxation during a refraction process. It can advantageously be cumulated with the above mentioned steps a), b), c) of the method according to the invention.

The method for inducing a controlled variation of accommodation in an eye of a subject may be in particular used in a method for determining at least a refraction feature of an eye of a subject according to the invention. This method implies achieving the method for inducing the controlled variation of accommodation according to the invention before achieving the usual visual test for determining the refraction features of the eyes. The eyes are then placed in an appropriate accommodative state for determining this refraction.

The accommodation may be relaxed if a test in far vision is achieved, and may be stimulated if a test in intermediate or near vision conditions is required.

It is also possible to consider a method using the method for inducing a controlled variation of accommodation in an eye of a subject according to the invention, wherein a step of determining in real time the accommodation of eye of the subject is performed while the subject observes the target moving in step c), and, depending on the accommodation of the eye determined, modifying in real time at least one feature of the target, in particular among the following features: position in the 2D image or 3D representation, position of the plane where the target is focalized, disparity of the target.

The method for controlling accommodation of the subject is particularly useful when performing a refraction determination test, such as a subjective refraction determination test. According to the invention, such a method comprises the following steps:

a) displaying an environmental scene,
b) displaying, in this environmental scene displayed in step a), a target visible by the subject through said optical system, said target being displayed in such a way that it is perceived by the subject as moving away from said subject or moving towards the subject,
c) having the subject observe said target moving displayed in step b) and
d) assessing the visual performance of the subject after the subject has observed the target moving in step c),
e) determining said refraction feature based on the assessment of step d).

In practice, as described above, the displaying of the target in step b) inducing the perception of a moving target may be obtained using one or more of the following:

modifying the size of the target displayed,
modifying the position of the target displayed relative to the environmental scene,
moving the focalization plane of the target,
modifying the position in space of the target relative to the subject, in particular the distance between the target and the subject,
changing the disparity of the target in a stereoscopic display, that is to say, when using a stereoscopic displaying device.

The steps c) and d) may be performed according to any known method of determination of the refraction, in particular subjective determination of the refraction. Thanks to the method for inducing a controlled variation of accommodation, the subject may be placed in conditions of relaxed accommodation or increased accommodation prior to the performance of these steps c) and d).

The invention also relates to the global display for inducing a controlled variation of accommodation in an eye of a subject, comprising said environmental scene and said target displayed within this environmental scene, said target being displayed in such a way that it is perceived by the subject as moving away from said subject or moving towards said subject within said environmental scene.

For example, said global display can be the one belonging to a device as disclosed in the patent application EP 3298952, incorporated herewith as reference, comprising an acuity module and a scene module with corresponding screens and an optical system such as a beam splitter, making it possible to transmit the light beam produced by the acuity module, and to add in the same direction the light beam initially produced by the screen of the scene module, i.e. to combine the image produced by the acuity module with another image generated by the screen of the scene module. In this case, the above mentioned target is shown on the acuity screen, and the above mentioned environmental scene, is shown on the scene screen, showing to a subject an image resulting from the combination of both target and environmental scene.

This global display can be used in any embodiment of the method disclosed therein.

The invention claimed is:

1. A method for inducing a controlled variation of accommodation in an eye of a subject, using an optical system arranged in front of at least one eye of the subject including a global display with an acuity module and a scene module and an optical system configured to transmit a light beam produced by an acuity screen of the acuity module and a light beam produced by a scene screen of the scene module along a same direction, combining an image produced by the acuity screen with another image generated by the scene screen, and comprising:

a) displaying an environmental scene on the scene screen;
b) displaying a target on said acuity screen, such that the eye of the subject views an image resulting from the combination of the target and the environmental scene displayed in step a), said target being visible by the subject through said optical system, said target being displayed in such a way that it is perceived by the subject as moving away from said subject or moving towards said subject within said environmental scene; and
c) instructing the subject to observe said target displayed in step b), wherein, in steps a) and b), at least one of the environmental scene and the target is displayed using a stereoscopic device displaying two overlaid images of said at least one of the environmental scene and target, each image being seen by one of the eyes of the subject, said stereoscopic device introducing a spatial shift between the two images forming together a stereoscopic three-dimensional representation, and wherein, while said at least one of the environmental scene and target is displayed, said spatial shift between the two images of the stereoscopic three-dimensional representation seen by the eyes of the subject is progressively reduced or increased.

2. The method according to claim 1, wherein said environmental scene is perceived as stationary by the subject while the target is perceived as moving relative to the subject.

3. The method according to claim 1, according to which, in step b), an angular size of the target displayed is progressively reduced in order for said target to be perceived as moving away by the subject or increased in order for said target to be perceived as moving towards the subject.

4. The method according to claim 1, wherein, in step b), a position of the target displayed within the environmental scene is modified progressively.

5. The method according to claim 1, wherein, in step a), the environmental scene (1) comprises a two-dimensional image or a three-dimensional representation.

6. The method according to claim 1, wherein one of the two images of the stereoscopic three-dimensional representation is shifted spatially compared to a second one of these two images with a spatial shift corresponding to a disparity comprised between 1 and 20 prismatic diopters, the disparity being the same for both environmental scene and target or being different.

7. The method according to claim 1, wherein said spatial shift is strictly higher or strictly lower than an average spatial shift resulting from spacing between the eyes of the subject.

8. The method according to claim 6, wherein said two images of the stereoscopic three-dimensional representation are displayed for each eye of the subject using two different main colors or using different polarization or using a shutter system.

9. The method according to claim 1, wherein said environmental scene spread over a wide field of view of more than 10 degrees and/or said target exhibits features with different spatial frequencies.

10. A method for determining at least a refraction feature of an eye of a subject by performing the method for inducing a controlled variation of accommodation in an eye of a subject according to claim 1, wherein the method further comprises:
   d) assessing visual performance of the subject after the subject has observed the target moving in step c); and
   e) determining said refraction feature based on the assessment of step d).

11. A display for inducing a controlled variation of accommodation in an eye of a subject, comprising:
   a global display with an acuity module and a scene module, wherein
   said scene module includes a scene screen for displaying an environmental scene,
   said acuity module includes an acuity screen for displaying a target; and
   an optical system being configured to transmit a light beam produced by said acuity screen and a light beam produced by said scene screen along a same direction, combining an image produced by the acuity screen with another image generated by the scene screen, said target being surrounded by said environmental scene and visible by the subject through said optical system in such a way that it is perceived by the subject as moving away from said subject or moving towards said subject within said environmental scene,
   within said environmental scene,
   wherein at least one of a device for displaying the environmental scene and an optical device for displaying the target uses a stereoscopic device displaying two overlaid images of said at least one of the environmental scene and target, each image being seen by one of the eyes of the subject, said stereoscopic device introducing a spatial shift between these two images forming together a stereoscopic three-dimensional representation,
   and wherein, while said at least one of the environmental scene and target is displayed, said spatial shift between the two images of the stereoscopic three-dimensional representation seen by the eyes of the subject is progressively reduced or increased.

12. An optical system for inducing a controlled variation of accommodation in an eye of a subject when arranged in front of at least one eye of the subject, comprising:
   a global display with an acuity module and a scene module, wherein
   said scene module includes a scene screen for displaying an environmental scene,
   said acuity module including an acuity screen for displaying a target and said optical system being configured to transmit a light beam produced by said acuity screen and a light beam produced by said scene screen along a same direction, combining an image produced by the acuity screen with another image generated by the scene screen, said target being surrounded by said environmental scene and visible by the subject through said optical system
   in such a way that it is perceived by the subject as moving away from said subject or moving towards said subject within said environmental scene,
   wherein at least one of a device for displaying the environmental scene and an optical device for displaying the target uses a stereoscopic device displaying two overlaid images of said at least one of the environmental scene and target, each image being seen by one of the eyes of the subject, said stereoscopic device introducing a spatial shift between these two images forming together a stereoscopic three-dimensional representation, and
   wherein, while said at least one of the environmental scene and target is displayed, said spatial shift between the two images of the stereoscopic three-dimensional representation seen by the eyes of the subject is progressively reduced or increased.

13. The optical system according to claim 12, wherein said environmental scene is focused in a first focal plane, said target is displayed in a second focal plane, and said optical system includes a command circuit adapted to command movement of said first focal plane and/or a second focal plane in an independent manner, continuously or discontinuously.

* * * * *